United States Patent [19]

Suzuki

[11] Patent Number: 4,508,057
[45] Date of Patent: Apr. 2, 1985

[54] ALGAL CULTURING REEF UNIT, ARTIFICIAL REEF UNIT AND ARTIFICIAL CULTURING AND FISHING FIELD UNIT

[75] Inventor: Tetsuo Suzuki, Sabae, Japan

[73] Assignee: Tokyu Musashi Mfg. Co., Ltd., Tokyo, Japan

[21] Appl. No.: 533,024

[22] Filed: Sep. 16, 1983

[51] Int. Cl.³ .............................. A01K 61/00
[52] U.S. Cl. ........................................ 119/3
[58] Field of Search ............ 119/2, 3, 4; 405/30, 405/33, 35

[56] References Cited

U.S. PATENT DOCUMENTS

| | | | |
|---|---|---|---|
| 3,704,687 | 12/1972 | Nohmura | 119/3 |
| 4,165,711 | 8/1979 | Aoki et al. | 119/3 |
| 4,196,694 | 4/1980 | Buchanan | 119/4 X |
| 4,316,431 | 2/1982 | Kimura | 119/3 |
| 4,431,337 | 2/1984 | Iwasa | 405/30 |

FOREIGN PATENT DOCUMENTS

| | | | |
|---|---|---|---|
| 2843391 | 4/1979 | Fed. Rep. of Germany | 119/3 |
| 2199438 | 9/1972 | France | |
| 2238428 | 2/1975 | France | 119/4 |
| 46129 | 11/1980 | Japan | 119/4 |
| 58-15572 | 4/1983 | Japan | |
| 918382 | 4/1982 | U.S.S.R. | 119/3 |

OTHER PUBLICATIONS

Petroleum Engineer International, vol. 54, No. 6, May 1982, Dallas D. J. Sheehy et al.

Primary Examiner—Robert P. Swiatek
Attorney, Agent, or Firm—Armstrong, Nikaido, Marmelstein & Kubovcik

[57] ABSTRACT

An artificial algal culturing reef unit, an artificial reef unit and an artificial culturing and fishing area unit, aimed at raising or culturing algae, fishes and shellfishes, are usually submerged in a shallow sea zone with a depth ranging between 5 and 15 meters. These units are required to be resistant to high waves and fast oceanic currents usually encountered in such sea zone. Although concrete materials are suitable in consideration of its strength and costs, an alkali is necessarily emitted from their surfaces that is extremely harmful to diatoms and algae as well as fishes and shellfishes. The present invention resides in an algal culturing reef unit and an artificial reef unit wherein a layer of iron sulfate or iron (II) sulfate or a layer of an acid and iron oxide powders are formed on the surface of concrete blocks for penetration into the inside of the blocks, whereby the alkali from the concrete is neutralized with an acid from the iron sulfate or iron (II) sulfate or an acid contained in said layer and iron oxides liked by algae or fishes and shellfishes are caused to exist in abundance on the reef surfaces.

9 Claims, 30 Drawing Figures

ALGAL CULTURING REEF UNIT, ARTIFICIAL REEF UNIT AND ARTIFICIAL CULTURING AND FISHING FIELD UNIT

BACKGROUND OF THE INVENTION

This invention relates to an algal culturing reef unit, an artificial reef unit and an artificial culturing and fishing area or field unit. More particularly, it relates to such units adapted for raising algae necessary for spawning and hatching of fishery products such as fishes, shellfishes and crustaceans and culturing and protection of the young fishes, shellfishes and crustaceans, and adapted for providing an environment suitable for raising these fishery products.

Recently, various artificial reef units have been developed and practiced for protection and raising of fishery products such as fishes and shellfishes. These units are intended for allurement of adult fishes and shellfishes for providing an artificial fishing field and are also termed as swarming reef. This type of reef may be realized by submerging used vessels, used cars, waste tires or concrete, steel, stone or synthetic resin materials assembled or molded into boxes or lattices.

On account of the recent tendency towards depletion of fishery resources and the problem of the 200-sea mile territory, there is an increasing demand for developing shore fishing. This has led to the development of the artificial reef unit aimed at raising or culturing fishery resources besides the aforementioned swarming reef. This culturing type reef is intended for protection and raising of larval and juvenile fishes and shellfishes.

For raising these juvenile marine animals, it is necessary to provide an environment suitable for settlement and growth of diatoms and other feed plants. Thus, in distinction from the swarming type reef, the culturing reef needs to be submerged in a shallow sea zone with a depth between 5 and 15 meters where there is sufficient supply of natural light beams. However, because of high waves and fast oceanic currents usually encountered in such sea zone, the culturing type reef is required to be sufficiently resistant to these severe environments.

Thus, the fishes and shellfishes would swim in water for a certain period after hatching and grow in size while grazing on diatoms or other sea weeds or microorganisms. The fishes and shellfishes are called juvenile in this stage of development. Thus the presence of diatoms and microorganisms is imperative for the growth of these young aquatic animals. For growth of diatoms, it is essential to supply a sufficient quantity of oxygen and sunlight. To this end, the culturing reef unit needs to be submerged in a shallow sea zone presenting adverse environments and hence needs to be arranged and constructed to withstand the severe operating environments.

From economic considerations, the reef unit is preferably made of concrete in order to resist the adverse conditions usually met in the shallow sea zone. However, when submerged in sea water, concrete units or blocks emit a strong alkali from their surface (pH value, about 13). This strong alkali thus emitted into the sea water acts to hinder the settlement or growth of green algae or diatoms or other microorganisms and occasionally may even kill them. When dead, these algae are converted into a layer of calcares known as arthrocalcares, this layer falling on the concrete surface and interfering with settlement and habitation of the algae. In order to prevent this, it is necessary to neutralize the strong alkali emitted from the concrete surface. However, there is not known so far a technology effective to meet such needs.

In addition, the basic culturing conditions are different from one aquatic animal to another because of differences in habit, feed and the manner of living. However, it may not be said that these basic culturing conditions have not been considered sufficiently with the known types of the artificial reef units or culturing and fishing reef units.

SUMMARY OF THE INVENTION

In view of the aforementioned status of the prior art, it is an object of the present invention to provide an artificial reef unit and a culturing fishing field unit making use of a number of artificial reef units according to which, for meeting the aforementioned basic culturing conditions, the main body of the algal culturing reef unit or the artificial reef unit is made of concrete in order to be resistant to high waves and fast oceanic current proper to the shallow zone in a manner so that the strong alkali emitted from the surface of the concrete block is effectively neutralized and iron oxide contents necessary for growth of algae and fishes or shellfishes are caused to exist in abundance on the surface of the concrete block.

According to the present invention, crystal blocks of iron sulfate or iron (II) sulfate are embedded below the surface of the concrete base whilst the concrete is not as yet cured. As the concrete is hardened, the crystal blocks are dissolved in the moisture yielded from the concrete so that a porous layer of iron sulfate or iron (II) sulfate is formed on the resulting recesses on the concrete surface, said layer penetrating into the inside of the concrete, and the strong alkali contained in the concrete being neutralized with the acid from the iron sulfate or iron (II) sulfate. Alternatively, after the concrete base block has hardened, a solvent consisting of a mixture of a small amount of acid such as sulfuric acid and iron oxide powders such as iron sulfate or iron (II) sulfate powders and a concrete penetrant in turn consisting of a surfactant is coated on the surface of the base block for forming a layer of iron oxide powders such as iron sulfate or iron (II) sulfate powders, said layer penetrating into the inside of the concrete base block, the acid of the iron sulfate or iron (II) sulfate or that contained in the solvent acting for neutralizing the concrete alkali. According to the invention, this technology is utilized for providing an artificial alga culturing unit, an artificial reef unit and an artificial culturing and fishing field unit.

BRIEF DESCRIPTION OF THE DRAWINGS

FIGS. 8 through 10 illustrate an example of an artificial reef unit according to the present invention, wherein

FIGS. 12 through 14 illustrate a modification of the artificial reef unit according to the present invention, wherein

FIG. 16 through 19 illustrate a settlement reef unit adapted for settlement of larval and juvenile fish and shellfish, wherein

FIGS. 20 through 22 illustrate a raising reef unit aimed at raising fish and shellfish, especially sea crayfish wherein

FIGS. 28 through 30 illustrate a culturing and fishing field unit aimed at culturing fish and shellfish, especially sea crayfish, wherein

DESCRIPTION OF THE PREFERRED EMBODIMENTS

Figure 1:
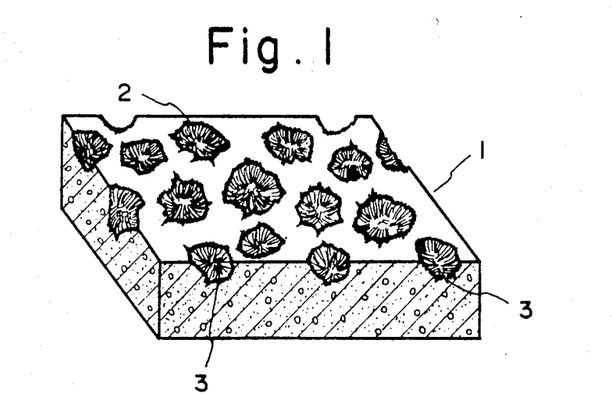
FIG. 1 is a perspective view showing a square base plate portion cut from a base plate used in the algal culturing unit of the present invention.

FIG. 1 shows in perspective a substantially square-shaped portion cut from a base plate used in a algal culturing reef unit embodying the present invention. In the figure, the numeral 1 designates a concrete base plate. Crystal blocks of iron sulfate or iron (II) sulfate are embedded below the surface of the base plate while the concrete is as yet not cured. As the concrete is hardened through curing, the crystals are dissolved in the water of the concrete for forming a number of pits or recesses 2 on the base plate surface. A layer 3 of iron sulfate or iron (II) sulfate is formed on the surface of the recess 2.

Figure 2:
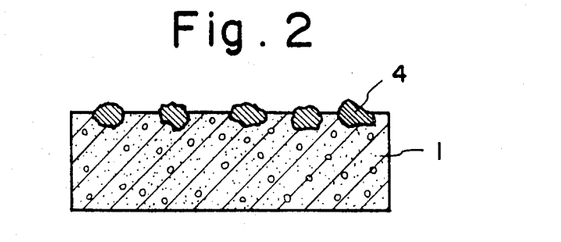
FIGS. 2 and 3 show a manufacture process thereof.
Figure 3:
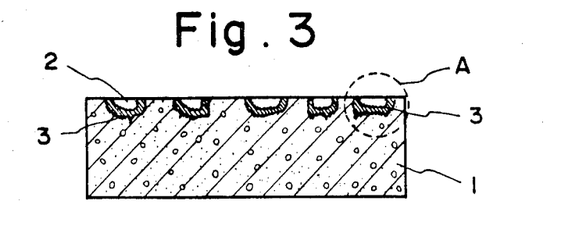

FIGS. 2 and 3 show in partial section the manufacture process of the aforementioned algal culturing base plate.

Figure 4:
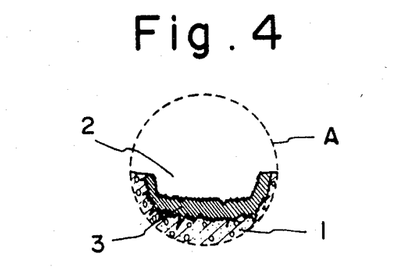
FIG. 4 is an enlarged view showing a portion A shown in FIG. 3.

The base plate 1 is cast by pouring mortar into a framework of any desired shape or structure, not shown. While the concrete of the base plate 1 is not hardened, a number of small-sized blocks 4 of iron sulfate or iron (II) sulfate are embedded, at least partially, below the base plate surface, as shown in FIG. 2, and the base plate 1 is cured in this state. During this curing stage, the concrete of the base plate 1 is dehydrated and hardened. On the other hand, the blocks 4 are dissolved in water yielded from the concrete for forming pits or recesses 2 shown in FIG. 3. On the surfaces of these recesses 2, there are formed porous layers 3 of iron sulfate or iron (II) sulfate, these layers 3 having extremely irregular upper surfaces as shown in FIG. 4 and reverse surfaces in contact with and penetrating into the inside of the concrete like the roots of the tree to resist peeling of the porous layers from the concrete surface.

Figure 5:
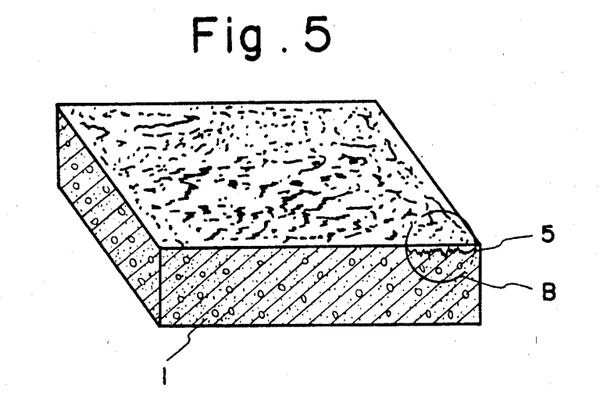
FIG. 5 is a perspective view showing a square portion of a modified base portion used in the algal culturing unit of the present invention.
Figure 6:
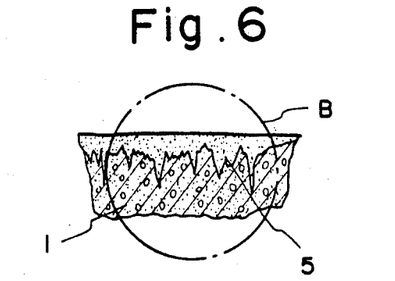
FIG. 6 is an enlarged view showing a portion B shown in FIG. 5.

In FIG. 5, a square piece of the base plate used in an algal culturing reef according to another embodiment of the present invention is shown in perspective. A solvent prepared by mixing comminuted particles of iron sulfate or iron (II) sulfate into a liquid concrete penetrant consisting of any suitable surface active agent is coated on the upper surface of the base plate 1. The iron sulfate or iron (II) sulfate particles penetrate from the surface into the inside of the concrete base plate due to the function of the surfactant. As shown in FIG. 6, which is a detailed sectional view showing a portion surrounded in circle in FIG. 5, the iron sulfate or iron (II) sulfate particles are penetrated from the base plate surface like the tree roots, due to the function of the surfactant, thus providing a penetrated layer 5. These iron sulfate or iron II sulfate particles are preferably small in size so as to be penetratable into the concrete due to the assistive function of the surfactant. It has been found that a depth of penetration which is larger than 5 cm from the surface into the inside of the concrete may be realized with a particle size of 0.8 to 1 $\mu$m.

Alternatively, a solvent consisting of the concrete penetrant or surfactant and a mixture of fine particles of iron oxide less than 1 $\mu$m in size with a small amount of acid such as sulfuric acid may be used for providing the penetrated layer 5 consisting of the acid and the particles of iron oxide.

The penetrated layer 3 of iron sulfate or iron (II) sulfate on the base plate shown in FIGS. 1 and 5 is strongly acidic because of acid contents in the solvent or the iron sulfate and is capable of neutralizing the alkaline contents in the concrete of the base plate 1. Hence, when the aforementioned base plates are placed on the shallow sea floor either singly or as components of a variety of structural units, the concrete surface portions covered by the penetrated layers 3 or 5 are not exposed to sea water so that any alkaline contents emanating from the concrete are neutralized by the acid mixed in the solvent or that contained in iron sulfate or iron (II) sulfate and thus prevented from going into the sea water. In addition, since iron oxides are liked by algae and marine organisms, there is provided an environment highly suitable for settlement and growth of sea plants grazed by the marine organisms, such as algae or green algae.

Figure 7:
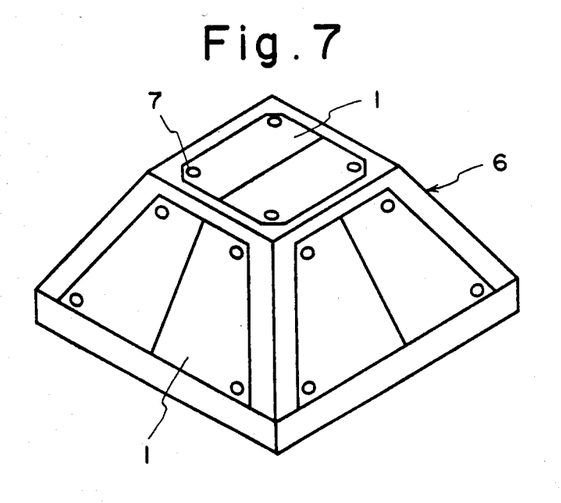
FIG. 7 is a perspective view showing an example of an artificial algal culturing reef unit of the present invention.

FIG. 7 shows an algal culturing reef unit consisting of a concrete block 6 in the form of a frustrum of a regular pyramid on each surface of which a piece of the base plate 1 shown in FIGS. 1 or 5 cut into a corresponding profile is secured with suitable fasteners 7 such as bolts and nuts. This reef unit is placed on the shallow sea bottom 5 to 10 meters deep where high waves or currents are encountered. The waves or currents striking the lateral sides of the block 6 flow upwards along the inclined surfaces of the block 6 thus giving rise to an upward turbulent flow of sea water. On account of such turbulent flow of sea water, there may be assured an abundant supply of oxygen and sunlight necessary for survival and growth of algae and aquatic organisms.

The applicant has conducted an experiment with the aforementioned algal culturing reef unit placed on the shallow sea bottom of the Japan Sea with the depth of 5 to 10 meters. It has been found that numerous sea plants such as green alga and kurome settled on the blocks in the winter six-month period of November to April and that shellfish such as abalone and top shells also settled on the blocks.

Figure 8:
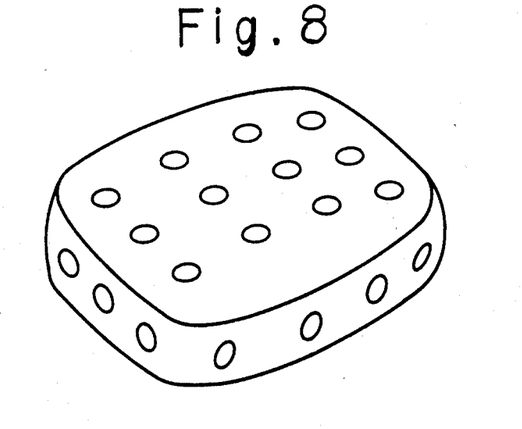
FIG. 8 is an overall perspective view of the reef unit.
Figure 9:
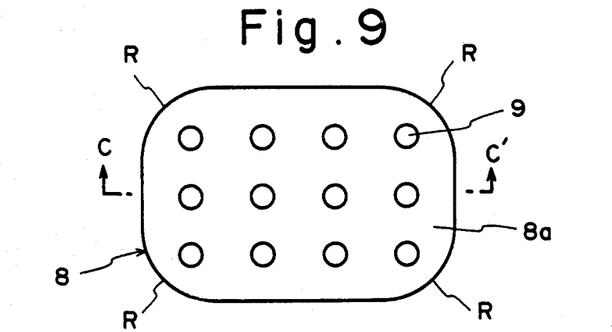
FIG. 9 is a plan view of the reef unit.
Figure 10:
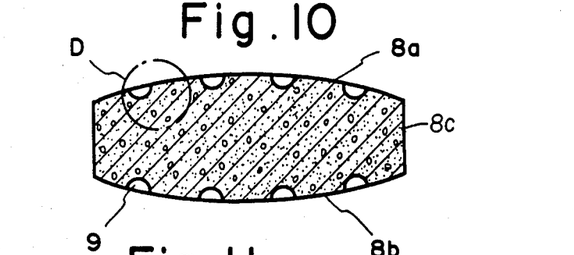
FIG. 10 is a sectional view taken along line C-C' of FIG. 9.
Figure 11:
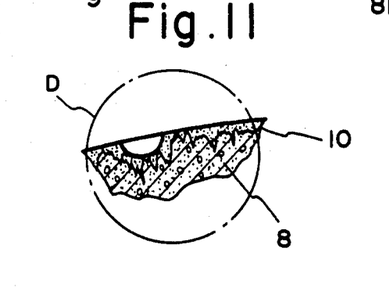
FIG. 11 is an enlarged view showing a portion D shown in FIG. 10.

FIG. 8 is an overall perspective view of an artificial reef unit embodying the present invention and FIG. 9 is a plan view thereof. As shown in FIG. 10, which is a section taken along line C-C' in FIG. 9, the convex upper and lower surfaces 8a, 8b as well as lateral surfaces 8c of the block are provided with a number of hemispherical pits or recesses. The four corners of the rectangular block 8 are curved with a radius R. The surfaces of the concrete block 8 are coated with a solvent prepared by mixing fine particles of iron sulfate or iron (II) sulfate with a concrete penetrant consisting of a suitable surfactant, or a solvent prepared by mixing sulfuric acid and iron oxide powders less than 1 $\mu$m in size with a concrete penetrant. When the solvent is coated in this manner on the surface of the concrete block 8, a penetrating layer 10 of iron sulfate or iron (II) sulfate or of sulfuric acid and iron oxide powders is formed on the concrete block surface, as in the case of the base plate 1 of FIG. 5, due to the assistive function of the surfactant (see FIG. 11 showing a portion D of FIG. 10 to an enlarged scale). The layer 10 acts to neutralize the alkali emitted from the concrete, as mentioned hereinabove.

When the concrete block is placed on the sea floor, diatoms or algae tend settle on the block due to abundance of iron oxides and the aforementioned removal of the alkaline contents. Besides, sea urchins and shellfish swarm about the block to graze upon these diatoms or algae. In addition, the hemispherical recesses 9 provide the best habitation for them to find shelter from their enemies. It has been confirmed from the aforementioned experiment that the hemispherical recess 9 need be of a size to conform to the habitation of the sea urchins and shellfish and that the diameter of the recess approximately equal to 5 cm is preferred for the sea urchins or shellfish to survive and to defend their territory against invaders. The recess 9 need not be hemispherical but may also be of any other shape such as box shaped, provided that such shape of the recess has been found to be suitable for habitation of the aquatic animals.

As a result of the applicant's prolonged research on the habit and manner of living of sea urchins and shellfish, especially sea urchins, and the kinds of plants grazed upon by them, the artificial reef unit shown in FIG. 8 has been confirmed as satisfying certain basic culturing conditions. Thus, it has been found that abundant algae settle on the surface of the block 8 and each recess 9 is occupied by one sea urchin. The recesses 9 on the lower side of the block 8 provide good habitations for young sea urchins and shellfish finding shelter from their enemies and are extremely useful to prevent depletion of sea urchins and shellfish.

Figure 12:
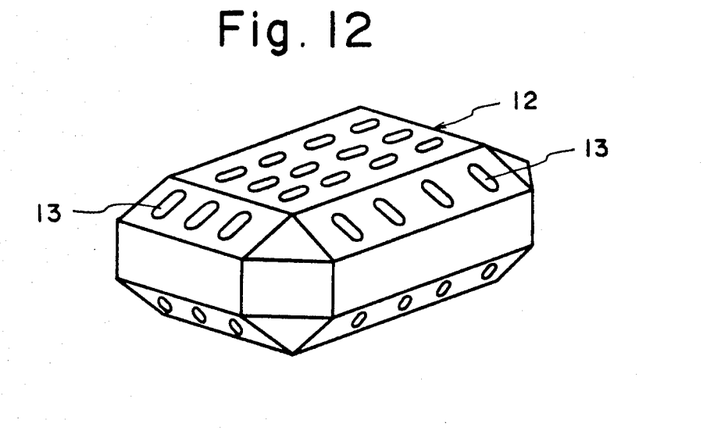
FIG. 12 is an overall perspective view of the reef unit.
Figure 13:
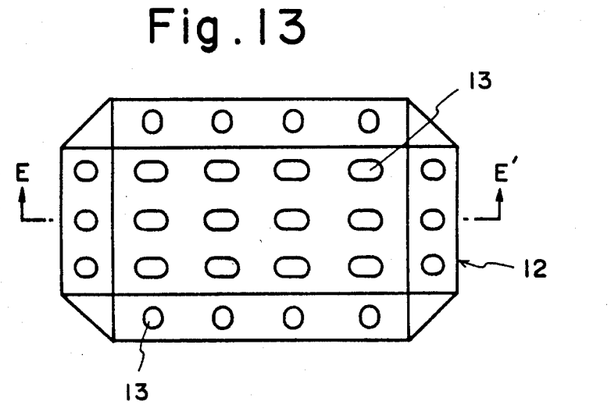
FIG. 13 is a plan view of the reef unit.
Figure 14:
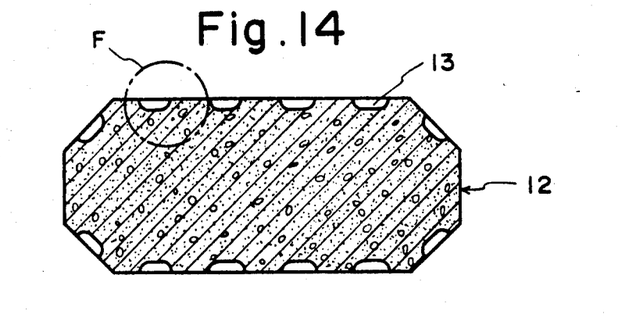
FIG. 14 is a sectional view taken along line E-E' of FIG. 13.
Figures 15, 16:
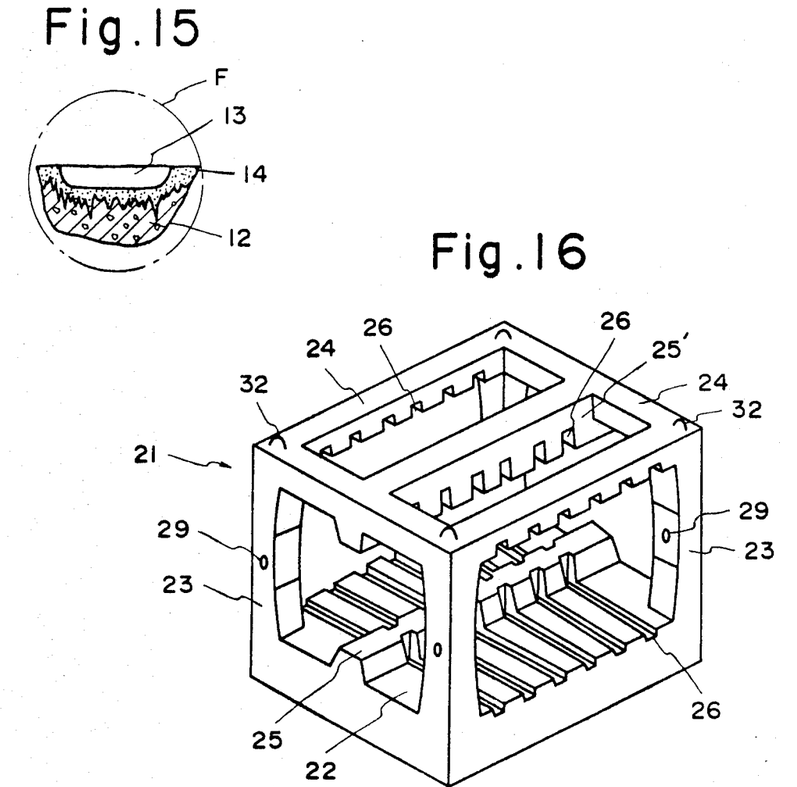
FIG. 15 is an enlarged view of a portion F in FIG. 14.
FIG. 16 is a perspective view of a reef frame.

FIG. 12 shows an artificial reef unit according to a modified embodiment of the present invention and especially designed for culturing abalone and top shells. FIG. 13 is a plan view of the reef unit and FIG. 14 is a sectional view taken along line E-E' of FIG. 13. There is shown a multisided concrete block 12 providing the artificial reef unit of the present embodiment and presenting respective eight sides when seen in plan view and side elevation, the block 12 thus providing twenty-six flat sides. The block 12 is provided with numerous oblong recesses 13 on the upper five sides and the lower five sides as shown. These ten surfaces of the concrete block 12 are coated with a solvent consisting of a mixture of fine powders of iron sulfate or iron (II) sulfate with a concrete penetrant consisting in turn of a surfactant, or a solution consisting of a mixture of a concrete penetrant with sulfuric acid and fine powders of iron oxide less than 1 $\mu$m in diameter. When coated in this manner with the solvent, the surfaces of the concrete block 8 are formed with a penetrated layer 14 of iron sulfate or iron (II) sulfate or of acid and fine powders of iron oxides as in the case of the base plate 1 shown in FIG. 5 (see FIG. 15 showing a portion F of FIG. 14 to an enlarged scale) thus neutralizing the alkaline contents otherwise emitted from the concrete. Besides, the layer 14 provides a good habitation for settlement of algae or diatom when the block is placed on the sea floor, in the same manner as discussed above in connection with the embodiment shown in FIG. 8.

In contradistinction to sea urchins, abalone and top shell, especially abalone, are extremely sensitive and escape from their habitation when the reef unit on which they rest is subjected to only slight vibration caused by wave motion. It is therefore imperative that the reef unit be resting stably on the sea floor. The multisided body shown in FIG. 12 is preferred in point of stability to the block shown in FIG. 8 presenting a curved surface. Abalone and top shell are different in shape, although approximately equal in crust size. In general, abalone prefer to rest in recessed places on the rock surface, while the top shells tend to attach on the back side of the rock. Thus, when the multisided block 12 shown in FIG. 12 is placed on the surface of the sea floor, the top shells rest on the recesses 13 on the upper five surfaces, whereas abalone attach to the recesses 13 on the lower five surfaces. It has been found that the oblong recess 13 is preferably 8.5 cm in longer diameter, 5.0 cm in shorter diameter and about 5.0 cm in depth. The recesses need not be oblong but may be of any other shape such as box shape provided that such shape of the recesses is found to be suitable for the abalone and top shell to survive and defend their territory against invaders.

Figure 17:
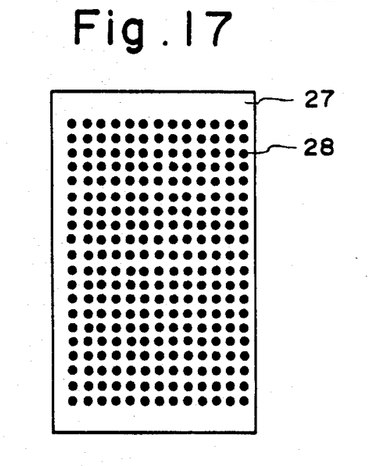
FIGS. 17 and 18 are front and side views of a flocked plate, respectively.
Figure 18:
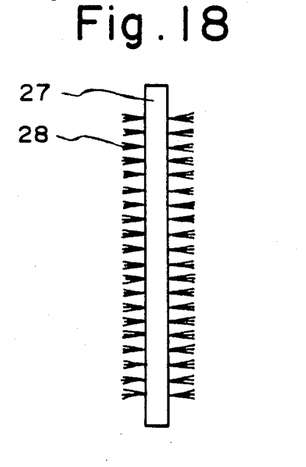
Figure 19:
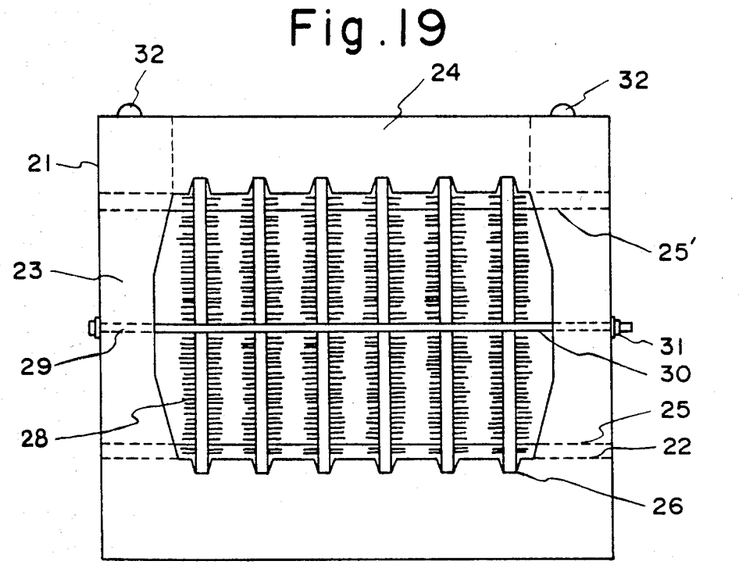
FIG. 19 is a front view of the settlement reef unit.

FIGS. 16 to 19 illustrate a settlement reef unit adapted for settling and raising larval and juvenile fishes and shellfishes. FIG. 16 is a perspective view of a frame, FIGS. 17 and 18 are front and side views, respectively, of a flocked plate and FIG. 19 is a front view of the reef unit. In the figures, the numeral 21 designates the frame comprised of a square bottom plate 22, four upright pillars 23 integrally formed with four corners of the bottom plate 22 and four girders 24 mounted across the upper ends of the girders 23. A central rib 25 is provided on the bottom plate 22 and a central rib 25' is also provided between the girders 24 in opposition to the lower rib 25. The bottom plate 22, the ribs 25, 25' and the girders 24 are formed with grooves generally indicated at 26.

A flocked plate 27 shown in the front view of FIG. 17 and in the side view of FIG. 18 is mounted in each of the grooves 26. On the sides of the flocked plate 27, except the side resting on the groove bottom, there are inserted pile yarns 28 consisting of natural or synthetic fiber.

The plate 27 is placed in the groove 26 of the frame 21, a bolt 30 is passed through each through-hole 29 in the pillars 23 and a nut 31 tightened for securing the flocked plate 27 to the frame 21. In this manner, the plate 27 may be secured against accidental removal from the groove 26 due to wave motion or under the effect of oceanic currents. Four hoist hooks 32 are provided, one at each corner of the frame 21, for hoisting and submerging the reef unit with the aid of a crane or the like.

The raising or culturing reef unit comprised of the frame 21 and flocked plates 27 attached to the grooves 26 of the frame 21 is shown in assembled state in the front view of FIG. 19. When the raising reef unit is placed on the surface of the sea floor, the flocked plates 27 and the pile yarns 28 inserted on the plates protect larval and young fish and shellfish from their enemies, while the pile yarns 28 provide a habitation for settlement of the spores of sea weeds, plankton or the lower animals or plants and swimming organisms. Since a space is provided in the central zone where there are provided the ribs 25, 25', an upwardly directed turbulent flow is provided in the area with abundant supply of oxygen thus providing good habitation for the larval and young fish and shellfish.

Figure 20:
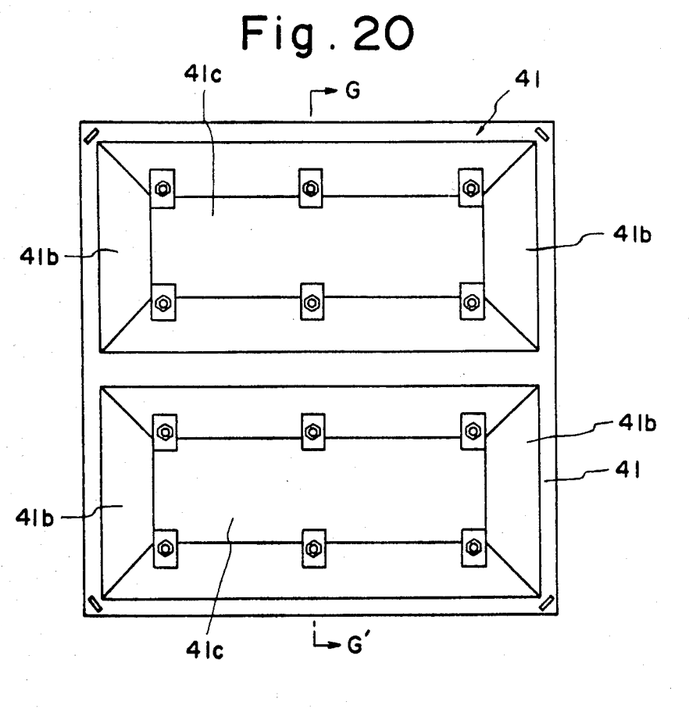
FIG. 20 is a plan view of the reef unit.
Figure 21:
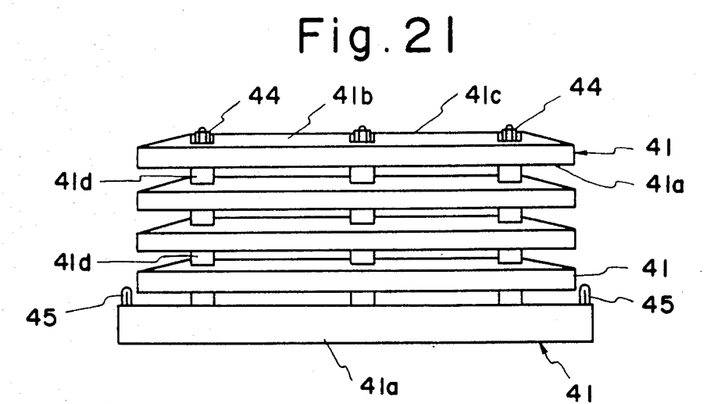
FIG. 21 is a front view of the reef unit.
Figure 22:
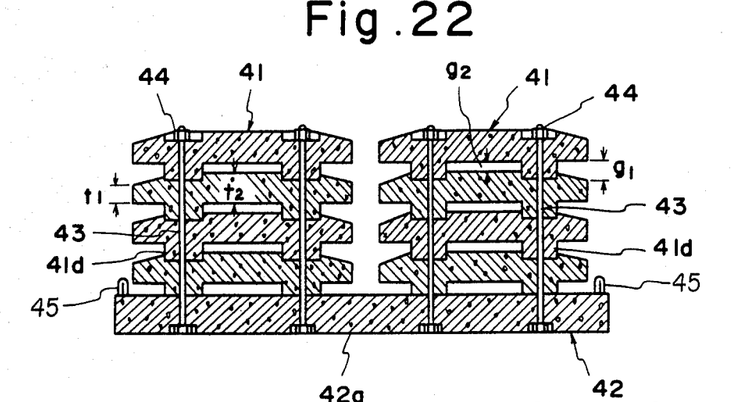
FIG. 22 is a sectional view taken along line G-G' of FIG. 20.

FIGS. 20 to 22 illustrate an example of a culturing reef unit for fish and shellfish, especially sea crayfish. FIG. 20 is a plan view of the reef unit, FIG. 21 a front view of the same and FIG. 22 a sectional view taken along line 20—20 of FIG. 20. In the drawing, the numeral 41 designates a generally flat plate-like concrete block presenting a rectangular shape when seen in plan view. The block 41 has a unitary flat lower surface 41a and an upper surface consisting of a flat central surface 41c and a tapered or inclined peripheral surface 41b. Therefore, the block 41 has a peripheral thickness $t_1$ lesser than the central thickness $t_2$ ($t_1 < t_2$). The block 41 is cast integrally with six square-sided concrete pillars 41d, these pillars being arranged in two rows of three pillars and extending vertically from the lower surface 41a of the block 41. The upper surface of the block 41 is formed with six mating recesses for receiving the six pillars 41d. The numeral 42 designates a concrete block which is to be the base block of the reef unit and of a size slightly larger than two blocks 41 placed side by side. The support block 42 has twelve recesses for receiving the pillars 41d of the concrete blocks 41.

Two concrete blocks 41 are placed side by side on the base block 42 in a manner so that the pillars 41d on the lower surfaces 41a of the blocks 41 are received in the mating recesses on the upper surfaces of the base block 42. Four blocks 41 are stacked one on the other, with the pillars 41d on the lower surfaces 41a of the block 41 being received in the mating recesses on the upper surfaces of the subjacent block 41. Six bolts 43 are then passed from the bottom surface of the base block 12 and through openings in the blocks 41 stacked on the base block 42 and openings in the pillars 41d. Finally, nuts 44 are attached to the ends of the bolts and tightened for securing the base block 42 and the four stacked blocks 41 together.

The numeral 45 designates hooks by means of which the reef unit can be hoisted with a crane for placement thereof on the surface of the sea floor. Four hooks are provided one at each corner of the base block 42.

The distance from the lower surface 42a of the base block 42 to the upper surface of the uppermost block 41 is preferably in the range of 1.5 to 2 m which is the usual range of activity or body movement of the sea crayfish. A central gap g2 between the adjoining blocks is selected in a manner so that the animal may hide itself against enemies and usually in the range of 7 to 20 cm depending on the animal size. A peripheral gap g1 between the adjoining blocks is selected in a manner so that the sea crayfish may enter therein without meeting substantial resistance.

In the above construction, the upper surface of the block 41 comprises the peripheral inclined surfaces 41b and the flat central surface 41c thus providing a streamlined profile for reducing the resistance presented to the sea water. The block 41 may have an increased central thickness t2 and an increased overall weight because the four-sided support pillars 41d are cast integrally with the concrete block, thus providing an extremely stabilized structure. The blocks 41 and the base blocks 42 are assembled to one another by six bolts 43 and nuts 44 with the pillars 41d received in the mating recesses thus providing a rigid structure resistant to vigorous wave motion usually encountered in the shallow sea zone.

Since the blocks 41 are made of concrete, an alkali contained in the concrete is emitted from the surface of the block 41 when the reef unit is submerged in the sea water. These alkaline contents are harmful to diatom, algae and sea animals and need be neutralized in the following manner.

Figure 23:
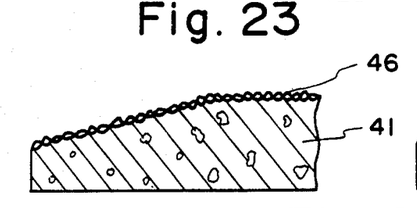
FIGS. 23 through 27 are partial sectional views showing manufacture process for the raising unit block.
Figure 24:
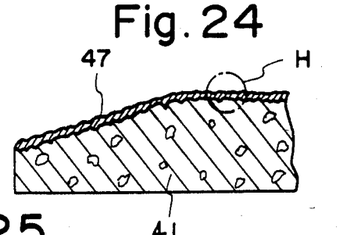
Figure 25:
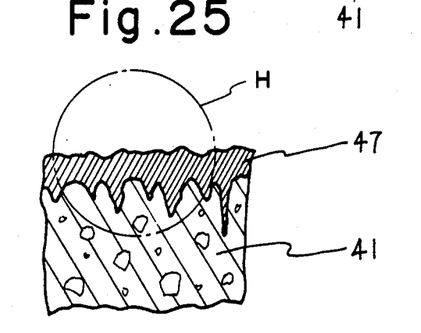

First of all, when the mortar is cast into the frame, not shown, for forming the block 41, a large number of iron sulfate or iron (II) sulfate crystal blocks are embedded below the surface of the cast mortar while the mortar is not as yet cured. As the concrete is cured and dehydrated, the crystals 46 are dissolved in water from the concrete for forming a porous layer 47 presenting an irregular surface as shown in FIG. 24. This penetrating iron sulfate or iron (II) sulfate layer 47 is rugged on its front surface as shown in the enlarged view of FIG. 25 and penetrated on its reverse surface into the inside of the concrete like the roots of a tree so that it is not peeled off readily from the concrete surface. This iron sulfate or the iron (II) sulfate layer is rich in weakly acidic iron oxide contents because the alkali in the concrete is neutralized with acid from iron sulfate.

Figure 26:
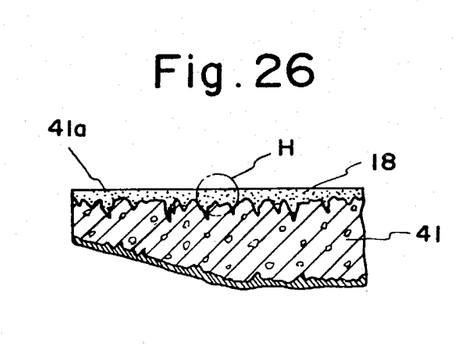
Figure 27:
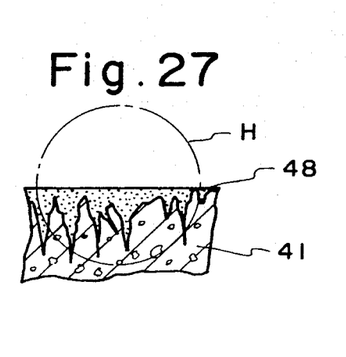

After the blocks 41 are hardened, the lower surface 41a of the block 41 is coated with a solvent consisting of a mixture of iron sulfate or iron (II) sulfate powders and a concrete penetrant consisting in turn of a surfactant. The iron sulfate or iron (II) sulfate powders are also penetrated from the surface into the inside of the concrete like the tree roots for providing a penetrating layer 48 as shown in an enlarged view of FIG. 27. It is preferred that the partial size of the iron sulfate or iron (II) sulfate powders be as small as possible.

The aforementioned solvent consisting of a mixture of iron sulfate or iron (II) sulfate powders and the concrete penetrant may be replaced by a solvent consisting of fine powders of iron oxide such as λ-iron oxide less than 1 μm in particle size, a small amount of sulfuric acid and a concrete penetrant consisting in turn essentially of surfactant. With the use of this solvent, sulfuric acid and iron oxide powders are penetrated from the surface into the inside of the concrete like tree roots due to adhesive function of the surfactant thus providing a penetrated layer 48 similar to the one shown in FIGS. 26 and 27.

The layer 48 is weakly acidic because the strong alkali (with pH approximately 13) contained in the concrete block 41 is neutralized with sulfuric acid in the solvent or with the acid yielded upon dissolution of iron sulfate or iron (II) sulfate.

With the use of the reef unit consisting of the base block 12 and the blocks 41 having the porous penetrated layer 47 derived from the iron sulfate or iron (II) sulfate crystals on the upper surface and the penetrating layer 48 derived from the solvent on the reverse surface, no alkalis are ejected from the surface of the block 41, while there is an abundant supply of iron ions sea crayfish.

Instead of providing the penetrated layer 47 derived from the iron sulfate or iron (II) sulfate powders and the layer 48 derived from the solvent on the upper and lower surfaces of the blocks 41, the penetrated layers 47, 48 may be provided on the reverse and front surfaces of the blocks, respectively. Alternatively, both surfaces of the block may be provided with porous layers 47 or with penetrated layers 48 from the solvent.

In the above embodiment, only one or three or more rows of concrete blocks 41 each consisting of plural tiers of blocks 41 may be mounted on the base block. Instead of sulfuric acid, any other acid capable of neutralizing the alkali in the concrete may be used. The tapered peripheral surfaces may be provided to the lower peripheral surface or to both the upper and lower peripheral surfaces of the concrete block.

Figure 28:
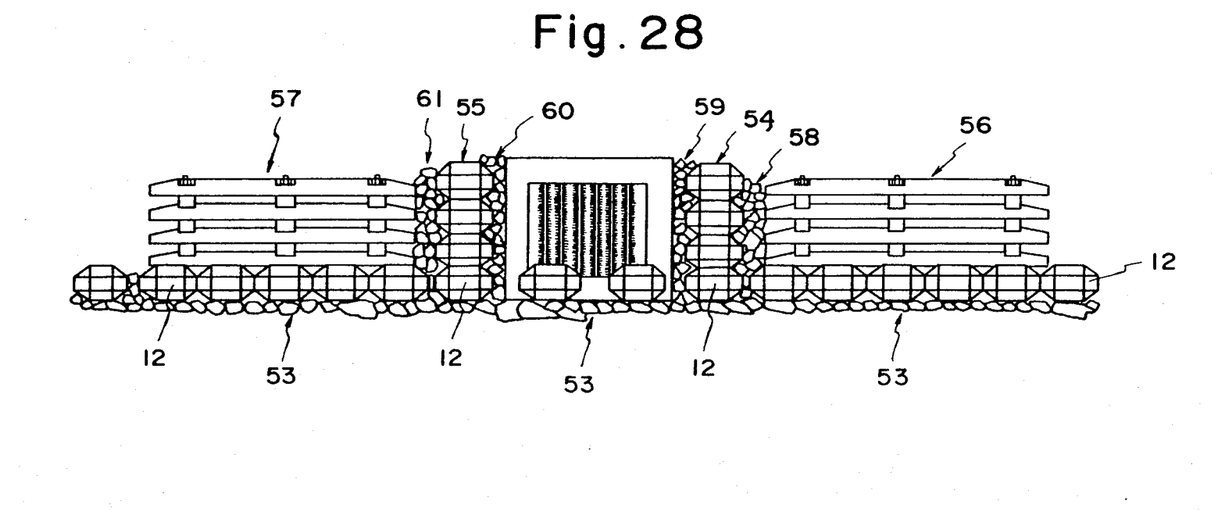
FIG. 28 is a front view of the field unit.
Figure 29:
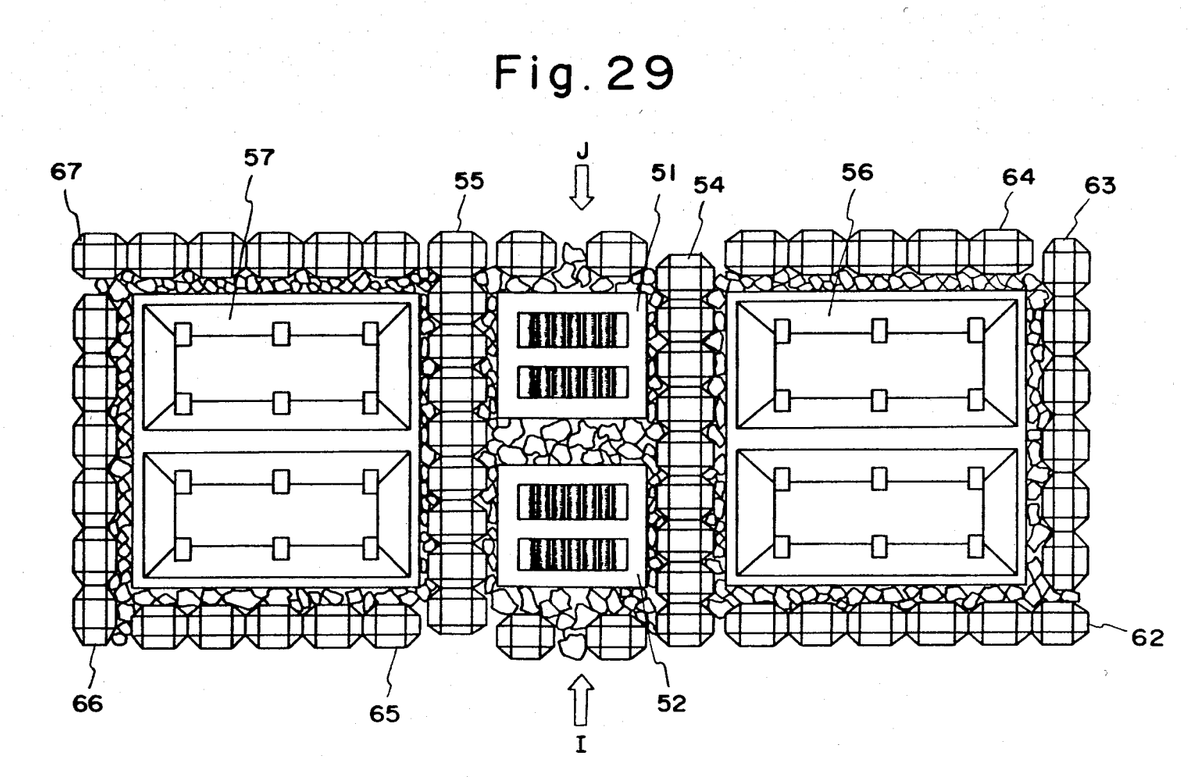
FIG. 29 is a plan view of the field unit.

FIGS. 28, 29 show an artificial culturing and fishing area unit for culturing fish and shellfish, especially sea crayfish, which is combined from the artificial reef unit shown in FIG. 12, the settlement reef unit shown in FIGS. 16 to 19 and the raising or culturing reef unit shown in FIGS. 20, 21. FIG. 28 shows the artificial fishing area unit. FIG. 28 is a front view and FIG. 29 a plan view of the unit. In the figure, the numerals 51, 52 designate settlement reef units similar to those shown in FIGS. 16 to 19 and on which larval or juvenile fishes and shellfish are settled. These reef units are arranged side by side on a bed of natural pebbles. On both sides of and adjacent to these two reef units 51, 52, plural reef blocks 12 as shown in FIG. 8 are stacked for forming block partitions 54, 55. To the outside of these block partitions 54, 55 are placed raising reef blocks 56, 57 for raising the sea crayfish as shown in FIGS. 20, 21. Natural pebbles are placed in the interstices between the reef blocks 51, 52 and the interstices between the block partitions 54, 55 for providing natural pebble partitions 59, 60. Natural pebbles are also stacked in the interstice between the raising reef block 56 and the block partition 54 and in the interstice between the raising reef block 57 and the block partition 55. Reef blocks 12 shown in FIG. 12 are placed around the raising reef blocks 56, 57 in block rows 62 to 67.

With the use of the reef blocks 12 each weighing about 500 kg and the block partitions 54, 55 each weighing about 18 tons, settlement reef blocks 51, 52 can be fixed stably.

The sea water flows into the reef in the direction shown by arrow marks I or J in FIG. 29 under the effect of wave motion or oceanic currents, thus producing an upwardly directed turbulent flow at the central zone. Thus the fish and shellfish, especially the larval and young sea crayfish living in the sea water are affixed to and settled on settlement blocks 51, 52. The larval or young sea crayfish graze on diatoms and plant or animal plankton deposited on settlement blocks 51, 52, block partitions 54, 55 on both sides of the blocks 51, 52 and the partitions 58 to 61 of natural pebbles.

It is known that sea crayfish are fond of iron ions because they find their habitation near the sunken vessel or on the rock abundant in ferrous contents. The sea crayfish are nocturnal animals and forage for food during night but hide themselves under the pebbles or between the rocks during daytime. Their favorite foods are shellfishes. As sea crayfish grow in size, they change their habitat from settlement blocks 51, 52 to the raising blocks 56, 57. The interstices g2 between the blocks 41, 41 shown in FIGS. 20 and 21 constituting the settlement blocks 56, 57 are equal to the gap between the rocks in which the sea crayfish rest during daytime, and provide a place where there is abundant supply of ferrous ions liked by sea crayfish. Thus they move to the raising blocks 56, 57 from settlement blocks 51, 52 as the animals grow to the adult stage.

In addition, sea weeds of various kinds grow on the rows 62 to 67 of the reef blocks 12 provided about the raising blocks 56, 57 so that abalone, top shell and other shellfish grazing on these sea weeds find their habitation about these blocks 12, the sea crayfish in turn foraging on these shellfishes. Hence, the artificial fishing area unit represents a culturing zone best suited for the sea crayfish.

Figure 30:
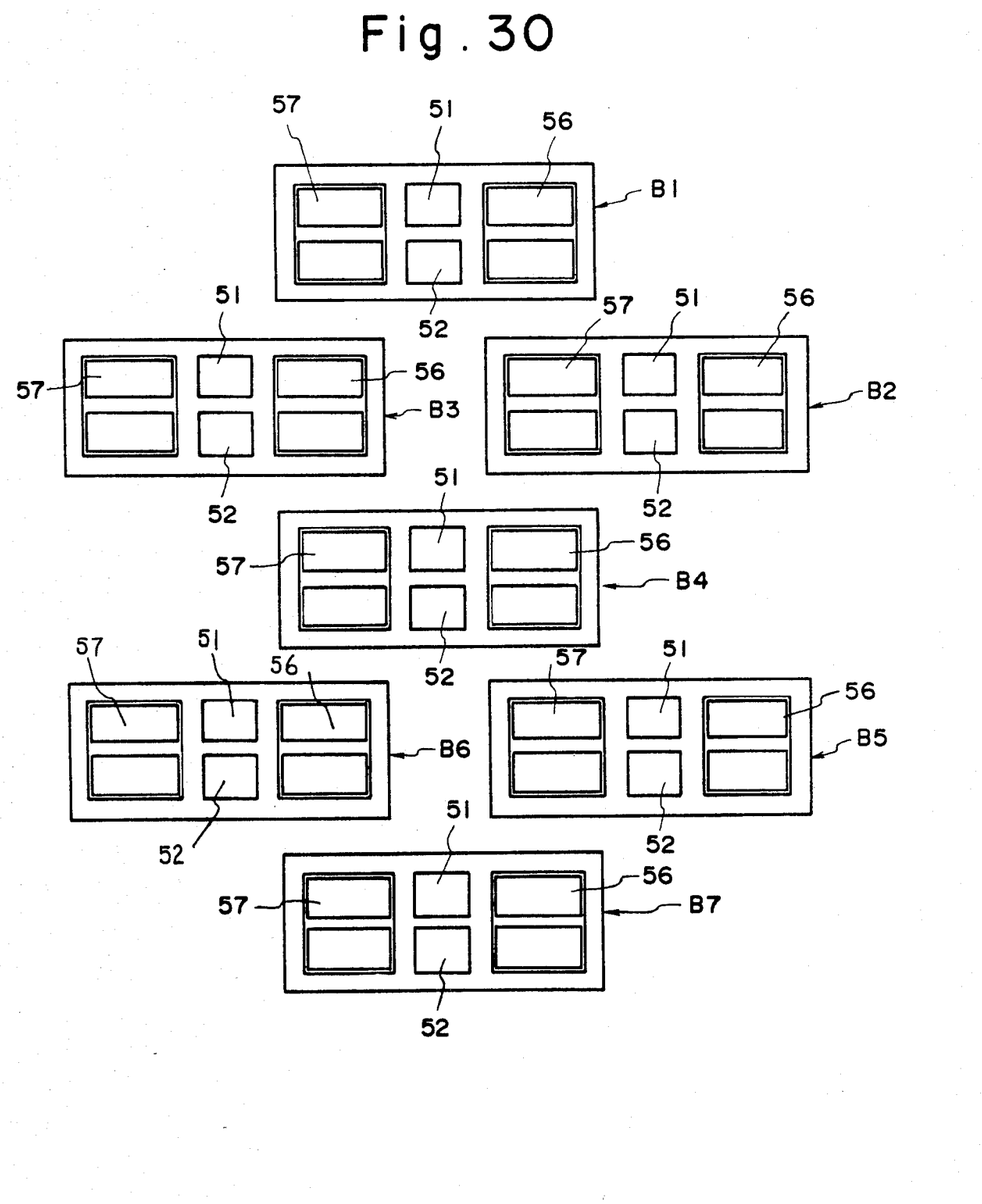
FIG. 30 is a schematic view of a culturing and fishing field unit combined from a plurality of fishing field units shown in FIGS. 28, 29.

FIG. 30 shows an example of a combined artificial fishing area consisting of a plurality of artificial fishing area units described hereinabove. In the figure, the combined artificial fishing area unit is composed of seven fishing area units B1 through B7 with each unit B1 through B7 consisting of settlement blocks 51, 52 and raising blocks 56, 57 as shown in FIG. 29. The unit B1 is arranged with respect to the units B2, B3 in a manner so that settlement blocks 51, 52 of the unit B1 are located close to the raising blocks 56, 57 of the units B2, B3. Similarly, the unit B4 is placed with respect to the units B2, B3, B5 and B6 in a manner so that settlement blocks 51, 52 of the unit B4 are located close to the raising units 56, 57 of the units B2, B3, B5 and B6, while the unit B7 is placed with respect to the units B5, B6 in a manner so that settlement blocks 51, 52 of the unit B7 are located close to the raising blocks 56, 57 of the units B5, B6. By thus combining the units B1 through B7, there is provided an extensive artificial fishing area unit in which sea crayfish may defend themselves against enemies and find sufficient food in the course of their lifetime since hatching from larvae until they grow to adults through the larval and juvenile stages.

In the above embodiment, the artificial fishing area unit shown in FIGS. 29 or 30 is composed of settlement reef units shown in FIGS. 16 through 19, the raising reef units shown in FIGS. 20, 21 and artificial reef units shown in FIG. 12, this is not limitative of the present invention. Instead, the fishing area unit may be composed of various other forms of the artificial reef units, raising reef units and settlement reef units that may be included within the scope of the present invention.

What we claim is:

1. A algal culturing reef unit comprising one or more concrete base blocks each having a multiplicity of recesses on at least one surface thereof, said at least one surface being covered with a layer of iron sulfate or iron (IT) sulfate that penetrates into the inside of the body of the concrete, said layer being formed by having iron sulfate or iron (II) sulfate crystal blocks embedded or buried in the body of the concrete from the at least one surface thereof while the concrete is not hardened, said crystal blocks being dissolved in the water contents of the concrete as the concrete is hardened.

2. An algal culturing reef unit comprising one or more concrete base blocks, wherein a solvent consisting of an acid and fine powders of iron oxide mixed into a concrete penetrant consisting essentially of a surfactant is coated on at least one surface of said one or more base blocks for providing a layer of acid and iron oxide powders on the at least one surface of said one or more blocks, said layer penetrating well into the body of the concrete.

3. An algal culturing reef unit as claimed in claim 2 wherein said solvent consists of fine powders of iron sulfate or iron (II) sulfate mixed into the concrete penetrant.

4. An artificial reef unit comprising one or more concrete blocks presenting a plurality of curved surfaces each provided with a multiplicity of recesses adapted for habitation by sea urchin and shellfish, wherein each curved surface is provided with a layer consisting of a mixture of acid, fine powders of iron oxide and a concrete penetrant in turn consisting essentially of a surfactant, said layer penetrating well into the body of the concrete.

5. An artificial reef unit comprising one or more concrete blocks presenting a plurality of curved surfaces each provided with a multiplicity of recesses suitable for habitation by shellfish, said curved surfaces being coated with at least one layer of acid and fine iron oxide particles mixed into a concrete penetrant consisting essentially of a surfactant, said at least one layer penetrating from the surface of the block well into the body of the concrete.

6. An artificial reef unit comprising a plurality of plate-like concrete blocks each presenting on one or both surfaces thereof a layer of iron sulfate or iron (II) sulfate, said plate-like blocks being stacked in one or more tiers and secured on a base block with a suitable interstice into which a sea crayfish may creep, said layer penetrating well into the body of the concrete.

7. An artificial culturing and fishing area unit comprising one or more settlement reef units on which larval and young shellfish can settle, one or more raising block units adjacent to said settlement units, and a plurality of artificial reef block units adjacent to said settlement units and raising block units and adapted for culturing algae and shellfishes each block unit having portions made of concrete, said portions presenting surfaces having at least one layer of a material selected from the group consisting of a mixture of acid and fine iron oxide particles and a concrete penetrant consisting essentially of a surfactant, sulfate, and iron (II) sulfate, the said at least one layer penetrating well into the concrete portions.

8. An artificial culturing and fishing area unit as claimed in claim 7, wherein each settlement reef unit is formed as a frame in which are fitted a number of flocked plates on which pile yarns are inserted.

9. An artificial culturing and fishing area unit as claimed in claim 7, wherein each artificial reef block unit is formed by a number of plate-like concrete blocks, said plate-like blocks being stacked in tiers on a base plate with a suitable distance between adjoining blocks and between the lowermost block and the base plate, the distance being selected to permit sea crayfish to creep inside the artificial reef block unit.

* * * * *